(12) United States Patent
Simpson et al.

(10) Patent No.: US 12,094,009 B2
(45) Date of Patent: *Sep. 17, 2024

(54) ELECTRONIC PHARMACY ADJUDICATION SYSTEM AND ASSOCIATED METHOD AND COMPUTER PROGRAM PRODUCT

(71) Applicant: Express Scripts Canada Co., Halifax (CA)

(72) Inventors: Michael Simpson, Toronto (CA); Chad Griffin, Burlington (CA)

(73) Assignee: Express Scripts Canada Co., Halifax (CA)

( * ) Notice: Subject to any disclaimer, the term of this patent is extended or adjusted under 35 U.S.C. 154(b) by 0 days.

This patent is subject to a terminal disclaimer.

(21) Appl. No.: 18/367,175

(22) Filed: Sep. 12, 2023

(65) Prior Publication Data

US 2023/0419415 A1  Dec. 28, 2023

Related U.S. Application Data

(63) Continuation of application No. 16/936,704, filed on Jul. 23, 2020, now Pat. No. 11,783,424.

(30) Foreign Application Priority Data

Jul. 31, 2019  (CA) .................................. CA 3051044

(51) Int. Cl.
| | | |
|---|---|---|
| *G16H 40/20* | (2018.01) | |
| *G06N 20/00* | (2019.01) | |
| *G06Q 20/20* | (2012.01) | |
| *G06Q 20/40* | (2012.01) | |
| *G06Q 30/018* | (2023.01) | |
| *G06Q 40/08* | (2012.01) | |

(Continued)

(52) U.S. Cl.
CPC .............. *G06Q 40/08* (2013.01); *G06N 20/00* (2019.01); *G06Q 20/202* (2013.01); *G06Q 20/405* (2013.01); *G06Q 30/0185* (2013.01); *G06Q 50/26* (2013.01); *G16H 20/10* (2018.01); *G16H 40/20* (2018.01); *G16H 70/40* (2018.01)

(58) Field of Classification Search
CPC .............................................. G06Q 50/20–26
See application file for complete search history.

(56) References Cited

U.S. PATENT DOCUMENTS 8,788,293 B2  7/2014  Kennedy
10,115,087 B2  10/2018  Pourfallah
(Continued)

*Primary Examiner* — Neal Sereboff
(74) *Attorney, Agent, or Firm* — Stinson LLP

(57) ABSTRACT

An electronic pharmacy adjudication system and associated method and computer program product for performing adjudication service for a healthcare insurance claim is provided. The system includes an interface layer, an orchestration layer and a service and rules engine layer configured for receiving, processing and releasing an adjudication decision. The orchestration layer processes the healthcare insurance claim to generate a sequence of service calls to the service and rules engine layer to derive a sequence of partial decision results, which are derived by processing a set of parameters identified by the service call according to a corresponding subset of decisions rules in a rules repository. The sequence of partial decision results is then processed to derive the adjudication decision corresponding to the healthcare insurance claim.

20 Claims, 8 Drawing Sheets

(51) Int. Cl.
*G06Q 50/26* (2012.01)
*G16H 20/10* (2018.01)
*G16H 70/40* (2018.01)

(56) References Cited

U.S. PATENT DOCUMENTS

| | | |
|---|---|---|
| 2011/0166872 A1 | 7/2011 | Cervenka |
| 2012/0109839 A1* | 5/2012 | Anderson .......... G06Q 10/1057 |
| | | 705/322 |
| 2012/0143634 A1 | 6/2012 | Beyda |
| 2013/0041676 A1* | 2/2013 | Momita ................ G06Q 50/18 |
| | | 705/2 |
| 2014/0257834 A1* | 9/2014 | Johnson ................ G06Q 40/08 |
| | | 705/2 |
| 2014/0304010 A1 | 10/2014 | Kennedy |
| 2014/0372143 A1 | 12/2014 | Kennedy |
| 2014/0379361 A1 | 12/2014 | Mahadkar |
| 2015/0006188 A1* | 1/2015 | Pummill ................ G06Q 40/08 |
| | | 705/2 |
| 2018/0018647 A1* | 1/2018 | Fredman ................ G06Q 50/22 |
| 2019/0279242 A1 | 9/2019 | Welch, Jr. |
| 2019/0287196 A1 | 9/2019 | Momita |

\* cited by examiner

ELECTRONIC PHARMACY ADJUDICATION SYSTEM AND ASSOCIATED METHOD AND COMPUTER PROGRAM PRODUCT

CROSS REFERENCE TO RELATED APPLICATIONS

This application is a continuation of U.S. patent application Ser. No. 16/936,704 filed Jul. 23, 2020, which claims priority to Canadian Application No. 3,051,044 filed Jul. 31, 2019, the entireties of which are hereby incorporated by reference.

TECHNICAL FIELD

The present invention relates generally to prescription drug benefits programs and more specifically relates to an improved healthcare insurance claims adjudication system and process for adjudicating consumer purchases that are covered by such programs.

BACKGROUND

Pharmaceuticals are usually sold through a third-party payment system in which pharmacies look directly to insurers or other obligors for primary payment. Pharmacies must rely on the payment practices and creditworthiness of third parties to collect for prescriptions provided to customers covered by a third-party payment plan.

The conventional prescription claims processing and payment system involves one or more entities providing one or more of a variety of functions. Generally, these parties include: the pharmacy, switch, processor and obligor.

In this context, a patient may make a claim under a health plan through the patient's pharmacy at the time the prescription is filled. Today most conventional pharmaceutical claims are adjudicated using an electronic on-line system. Pharmacies generally submit claims in real-time to a claims adjudication network for processing. Conventional systems for electronic claims adjudication by pharmacy benefits management ("PBM") companies have been around for some time. A PBM is an administrator of prescription drug programs. PBMs are primarily responsible for adjudication and paying claims for covered prescription drugs that are purchased by consumers who are members of the prescription drug benefit program. Other typical PBM services include developing and maintaining the drug formulary (the list of drugs covered by the prescription drug benefits program and their associated tiers), contracting with pharmacies, and negotiating discounts and rebates with drug manufacturers. Conventional PBM claim adjudication systems are typically employed when a member attempts to purchase a drug and the drug purchase is to be wholly or partially covered by a prescription drug benefits program. A prescription drug benefits program may be provided to the member through an employer health plan (e.g., ERISA plans, self-insured plans, managed care plans, Taft-Hartley trust plans, etc.), or a privately purchased health plan, a government sponsored plan (e.g., Medicare, Medicaid or any other city, state/province or local or federal government plan) or directly from a PBM provider. In such a transaction, the originating entity (e.g., a pharmacy) electronically transmits a claim to the PBM through a switch company for adjudication of the claim. The PBM adjudicates the claim to validate, among other things, that the member has a valid prescription drug benefits program, that the prescribing doctor is valid, and that the drug is covered by the prescription drug benefits program. The PBM sends an electronic response back to the pharmacy that denies the transaction or approves the transaction and also identifies the co-pay amount.

At a high level, the overall process of adjudicating drug purchase claims covered by the variety of prescription drug benefits programs offered under various types of health care plans is similar such that the pharmacy electronically transmits a claim to the PBM, the claim is adjudicated, and an electronic response is sent back to the pharmacy.

One challenge for systems implementing on-line adjudication processes for prescription drug purchase claims is that they are required to adjudicate very large number of claims within a reasonable delay to allow an insured user to receive an adjudication decision corresponding to the healthcare insurance claim when he is on location at a pharmacy filling his/her prescription. For example, Express Scripts Canada processes on average over 300,000 pharmacy claims per day, which annually translates to over 100 million claims. General guidelines required that each claim be processed in under 0.5 seconds.

In some cases, adjudication is performed using rules-based decision management systems. These systems comprise various logic rules that are configured to output decisions on the basis of data fed to the systems via one or more databases. In a typical system, an insurance claim is processed against many rules during the claim's adjudication lifecycle and the complexity of the rules can vary from simple to extremely complex. Patient historical data is typically required to process some of the claims adjudication rules and this data can be in the range of a current year, to many years of historical data. In the context of prescription drug purchase, databases that pertain to millions of users and span over decades may be required to provide full coverage of the adjudication service. As the complexity of the healthcare insurance claims increases, for example due to the number of possible combinations/conditions in the types of health benefits, the performance of these rules-based decision management systems is often unsatisfactory for generating adjudication decisions within the expected delays and, in some cases, these systems fail altogether. Dependencies between rules also create risk, complexity and make changes to rules more expensive. In typical pharmacy adjudication system there may be over 4,000 atomic rules in the adjudication system and the execution of these rules including information provided in the health insurance claim, plan design, and result of rules executed. As a consequence, the control and flexibility in the type of claims that can be electronically processed for adjudication is limited.

Against the background described above, it is clear that there remains a need in the industry to provide improved systems and methods for performing an adjudication service in connection with a healthcare insurance claim originating from a point of sale (POS) device that alleviate at least some of the deficiencies of the existing systems and methods.

SUMMARY

This Summary is provided to introduce a selection of concepts in a simplified form that are further described below in the Detailed Description. This Summary is not intended to identify key aspects or essential aspects of the claimed subject matter.

In accordance with a first aspect, an electronic pharmacy adjudication system is provided for performing an adjudication service in connection with a healthcare insurance claim originating from a point of sale (POS) device. The electronic pharmacy adjudication system includes one or more processors and a non-transitory computer readable memory storing computer program instructions. The computer program instructions when executed implement the following:
   a) an interface layer in communication with a data network configured for:
      i) receiving the healthcare insurance claim originating from the point of sale (POS) device, the healthcare insurance claim including a plurality of information data elements specifying characteristics of the healthcare insurance claim;
      ii) releasing results for transmittal to the point of sale (POS) device, the results conveying an adjudication decision corresponding to the healthcare insurance claim;
   b) a service and rules engine layer configured for:
      i) receiving a service call identifying a set of parameters on which the service call is to be applied; and
      ii) deriving a partial decision result at least in part by processing the set of parameters identified by the service call according to one or more decision rules from a rules repository, the one or more decision rules corresponding to the service call and being a subset of decisions rules in the rules repository;
   c) an orchestration layer in communication with said input interface layer and said service and rules engine layer, said orchestration layer being configured for:
      i) processing the information data elements in the healthcare insurance claim to generate a sequence of service calls and forwarding the service calls in the sequence of service calls to the service and rules engine layer to derive a sequence of partial decision results;
      ii) processing the sequence of partial decision results generated by the service and rules engine layer in response to the generated sequence of service calls to derive the adjudication decision corresponding to the healthcare insurance claim;
      iii) forwarding the derived adjudication decision to the interface layer for transmittal to the point of sale (POS) device.

Advantageously, the structure of the proposed electronic pharmacy adjudication system, which provides multiple interdependent layer including an orchestration layer and a service and rules engine layer, increases the flexibility in the type rules that can be applied and the manner in which they can be applied to healthcare insurance claim. In some implementation, that may facilitate the modification, removal and/or addition of new capabilities into the insurance claim adjudication lifecycle.

In some specific implementations of the above system, the plurality of information data elements in specifying characteristics of the healthcare insurance claim may include, without being limited to: patient information, insurance plan information and healthcare treatment information (such as for example drug prescription information), provider information, drug and drug pricing information.

In some specific implementations of the above system, the service and rules engine layer may be in communication with the rules repository, the rules repository containing business rules associated with healthcare insurance. The rules repository may be part of the electronic pharmacy adjudication system or may be an external module in communication with the service and rules engine layer of the electronic pharmacy adjudication system over a data network. In implementation in which the rules repository is part of the electronic pharmacy adjudication system, it may be stored on a computer readable storage medium. The specific contents of the data repository may vary between implementations and may include one or more rules that apply to a specific insurance carrier, including for example but without being limited to: core adjudication rules; legislative rules; rules pertaining to insurance programs developed by the specific insurance carrier and made available to all insurance carriers; and rules pertaining to insurance programs developed by the specific insurance carrier and only available to the specific insurance carrier.

In some specific implementations of the above system, the service and rules engine layer may also be in communication with a data repository containing health insurance information for a plurality of insured users. The data repository may be part of the electronic pharmacy adjudication system or may be an external module in communication with the service and rules engine layer of the electronic pharmacy adjudication system over a data network. In implementation in which the data repository is part of the electronic pharmacy adjudication system, it may be stored on a computer readable storage medium. The specific contents of the data repository may vary between implementations and may include, for example but without being limited to: insured party information; lists of drugs covered by the prescription drug benefits programs for at least some of the plurality of insured users; detailed coverage information; employment information; patient information including history; insurer; benefit plan; provider; prescriber; drug and drug pricing information; Drug Utilization Review (DUR). The specific content of the data repository is not critical to the invention and thus will not be described in further detail here.

In some specific implementations of the above system, the service and rules engine layer may be configured for processing the service call to identify in the rules repository the one or more decision rules corresponding to the service call and for executing the one or more decision rules identified in the rule repository to derive the partial decision result.

In some specific implementations of the above system, the service and rules engine layer may further be configured for processing the service call to identify in the data repository a data set for use by the service call and for deriving the partial decision result at least in part by processing data in the identified data set. For example, processing the service call to identify in the data repository a data subset for use by the service call may include processing the one or more decision rules to identify in the data repository a corresponding data subset required for each decision rule and executing each of the one or more decision rules at least in part by processing at least some of the set of parameters identified by the service call and the corresponding data subset.

In some specific implementations of the above system, the sequence of service calls generated by the orchestration layer may include one or more service calls selected from the set consisting of a claim validation service call, an eligibility verification service call, a benefit verification service call, a cost verification service call and a claim persistence service call.

In some specific implementations of the above system, the sequence of service calls includes at least a first service call and a second service call distinct from the first service call and the orchestration layer is configured for forwarding the first service call to the service and rules engine layer prior to transmitting the second service call to the service and rules engine layer.

In some specific implementations of the above system, the orchestration layer may be configured for processing the information data elements in the healthcare insurance claim to generate the sequence of service calls at least in part by:
  processing the information data elements in the healthcare insurance claim to derive a first service call;
  forwarding the first service call to the service and rules engine layer;
  in response to receipt of a partial decision result corresponding to the first service call, selectively generating a second service call at least in part by processing the partial decision result corresponding to the first service call.

Advantageously, generating a subsequent service call selectively, for example only when partial decision result of a previous service call make it relevant to perform the subsequent service call, allows making more efficient the adjudication process by omitting certain steps. For example, a specific implementation may have the first service call as including an eligibility verification service call and the second service call as including a benefit verification service call. If the partial decision result obtained from the eligibility verification service call indicates that the healthcare insurance claim does not satisfy the eligibility criteria (for example the identified insured party does not have drug coverage) then the orchestration layer would conclude that a second service call is not required to derive the (final) adjudication decision corresponding to the healthcare insurance claim and so the second service call would not be generated.

In accordance with another aspect, a method is provided for performing an adjudication service in connection with a healthcare insurance claim originating from a point of sale (POS) device. The method is implemented using one or more processors and a non-transitory computer readable memory storing computer program instructions. The method comprises:
  receiving the healthcare insurance claim from the point of sale (POS) device over a data network, the healthcare insurance claim including a plurality of information data elements specifying characteristics of the healthcare insurance claim;
  processing the information data elements in the healthcare insurance claim to generate a sequence of service calls to derive a sequence of partial decision results, wherein each service call in the sequence of service calls:
    identifies a set of parameters on which the service call is to be applied; and
    corresponds to one or more decision rules in a rules repository, the one or more decision rules being a subset of decisions rules in the rules repository;
  processing the sequence of partial decision results to derive the adjudication decision corresponding to the healthcare insurance claim;
  releasing results for transmittal over the data network to the point of sale (POS) device, the results conveying the derived adjudication decision corresponding to the healthcare insurance claim.

In some specific implementations of the above described method, deriving a specific partial decision result in the sequence of partial decision results associated with a specific service call may include processing a specific set of parameters identified by the specific service call according to one or more specific decision rules from the rules repository. The one or more specific decision rules correspond to the specific service call and are a specific subset of decisions rules in the rules repository. In such implementations, deriving the specific partial decision result in the sequence of partial decision results associated with the specific service call may include:
  processing the specific service call to identify in the rules repository the one or more specific decision rules corresponding to the specific service call; and
  executing the one or more specific decision rules identified in the rule repository to derive the specific partial decision result, wherein executing the one or more specific decision rules includes processing at least some parameters in the specific set of parameters identified by the specific service call.

In some other specific implementations of the above described method, deriving the specific partial decision result in the sequence of partial decision results associated with the specific service call may include:
  processing the specific service call to identify in a data repository a specific data set for use by the specific service call, the specific data set being a subset of data in the data repository;
  deriving the specific partial decision result at least in part by processing data in the identified specific data set and the specific set of parameters identified by the specific service call according to the one or more specific decision rules corresponding to the specific service call.

In some specific implementations, processing the specific service call to identify in the data repository the specific subset of data for use by the specific service call may include:
  processing the one or more specific decision rules to identify in the data repository a corresponding specific data subset for each specific decision rule amongst the one or more specific decision rules;
  executing each of the one or more specific decision rules at least in part by processing at least some of the set of parameters identified by the specific service call and the corresponding specific data subset.

In accordance with another aspect, a computer implemented method is provided for performing an adjudication service in connection with a healthcare insurance claim originating from a point of sale (POS) device. The method is implemented by one or more processors and a non-transitory computer readable memory storing computer program instructions and comprises:
  at an interface layer in communication with a data network, receiving the healthcare insurance claim originating from the point of sale (POS) device, the healthcare insurance claim including a plurality of information data elements specifying characteristics of the healthcare insurance claim;
  at an orchestration layer, processing the information data elements in the healthcare insurance claim to derive a sequence of partial decision results at least in part by generating a sequence of service calls to a service and rules engine layer;
  at the service and rules engine layer, for each service call in the sequence of service calls, deriving a corresponding partial decision result at least in part by processing a set of parameters identified by the service call according to one or more decision rules from a rules repository, the one or more decision rules corresponding to the service call and being a subset of decisions rules in the rules repository;
  at the orchestration layer, receiving and processing the sequence of partial decision results generated by the service and rules engine layer in response to the generated sequence of service calls to derive the adjudication decision corresponding to the healthcare insurance claim;

releasing results for transmittal over the data network to the point of sale (POS) device, the results conveying the derived adjudication decision corresponding to the healthcare insurance claim.

In accordance with another aspect, a computer program product is provided including computer program instructions stored on non-transitory computer readable memory. The program instructions when executed by one or more processors are configured for implementing an electronic pharmacy adjudication system of the type described above for performing an adjudication service in connection with a healthcare insurance claim originating from a point of sale (POS) device.

All features of exemplary embodiments which are described in this disclosure and are not mutually exclusive can be combined with one another. Elements of one embodiment or aspect can be utilized in the other embodiments/aspects without further mention. Other aspects and features of the present invention will become apparent to those ordinarily skilled in the art upon review of the following description of specific embodiments in conjunction with the accompanying Figures.

BRIEF DESCRIPTION OF THE DRAWINGS

A detailed description of specific exemplary embodiments is provided herein below with reference to the accompanying drawings in which.

Figure 1:
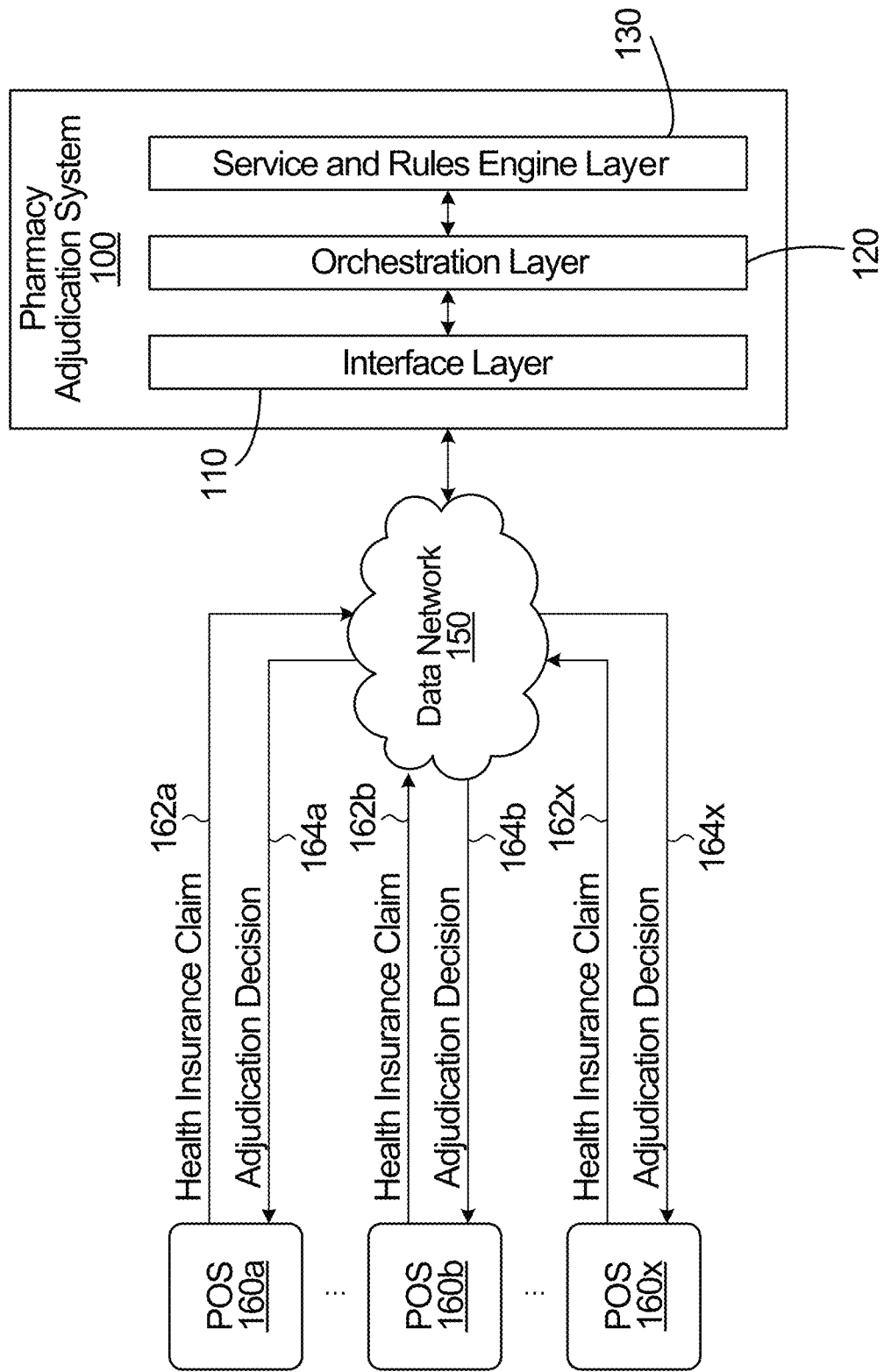
FIG. 1 shows a computer network including a pharmacy adjudication system 100 in accordance with a specific example of implementation of the invention in communication with a plurality of point of sale (POS) devices.

In the drawings, exemplary embodiments are illustrated by way of example. It is to be expressly understood that the description and drawings are only for the purpose of illustrating certain embodiments and are an aid for understanding. They are not intended to be a definition of the limits of the invention.

DETAILED DESCRIPTION

A detailed description of one or more specific embodiments of the invention is provided below along with accompanying Figures that illustrate principles of the invention. The invention is described in connection with such embodiments, but the invention is not limited to any specific embodiment. The scope of the invention is limited only by the claims. Numerous specific details are set forth in the following description in order to provide a thorough understanding of the invention. These details are provided for the purpose of describing non-limiting examples and the invention may be practiced according to the claims without some or all of these specific details. For the purpose of clarity, technical material that is known in the technical fields related to the invention has not been described in great detail so that the invention is not unnecessarily obscured.

The present invention relates generally to prescription drug benefits programs and more specifically relates to an improved claims adjudication system and process for adjudicating consumer purchases that are covered by such programs. "On-line adjudication" refers generally to the process by which a pharmacy electronically submits a healthcare insurance claim for reimbursement for a prescription and receives approval or disapproval of the healthcare insurance claim electronically. The healthcare insurance claim is approved or disapproved by a "processor," which is any entity that provides on-line adjudication. For example, the processor can be a PBM that facilitates on-line adjudication of drug benefits on behalf of employers or insurance companies providing workers' compensation coverage. As used herein, the term "healthcare insurance claim" refers generally to a claim for payment of costs associated with a healthcare prescription, including for example but without being limited to, claims submitted for prescription drug benefits under a health plan or workers' compensation system, claims submitted for dental benefits and the likes. In FIG. 1 a computer network is shown including a pharmacy adjudication system 100 in accordance with a specific example of implementation of the invention. As depicted, the pharmacy adjudication system 100 is communication with a plurality of point of sale (POS) devices 160a-x over a data network 150. It is appreciated that the pharmacy adjudication system 100 may receive healthcare insurance claims from a plurality of POS devices 160x and that "x" may be any suitable number. The POS device 160x may be any suitable computing device configured for establishing communication with data network 150 for entering in a data exchange for resolving a healthcare insurance claim. In a typical interaction, a specific point of sale (POS) device, such as POS device 160a, would transmit a healthcare insurance claim 162a, which would then be received by the pharmacy adjudication system 100 over data network 150. The received healthcare insurance claim 162a originating from the specific point of sale (POS) device 160a includes a plurality of information data elements specifying characteristics of the healthcare insurance claim. The pharmacy adjudication system 100 is configured for processing the healthcare insurance claim 162a to derive an adjudication decision corresponding to the healthcare insurance claim and for releasing such results 164a for transmittal to the point of sale (POS) device 160a through the data network 150.

Figure 2:
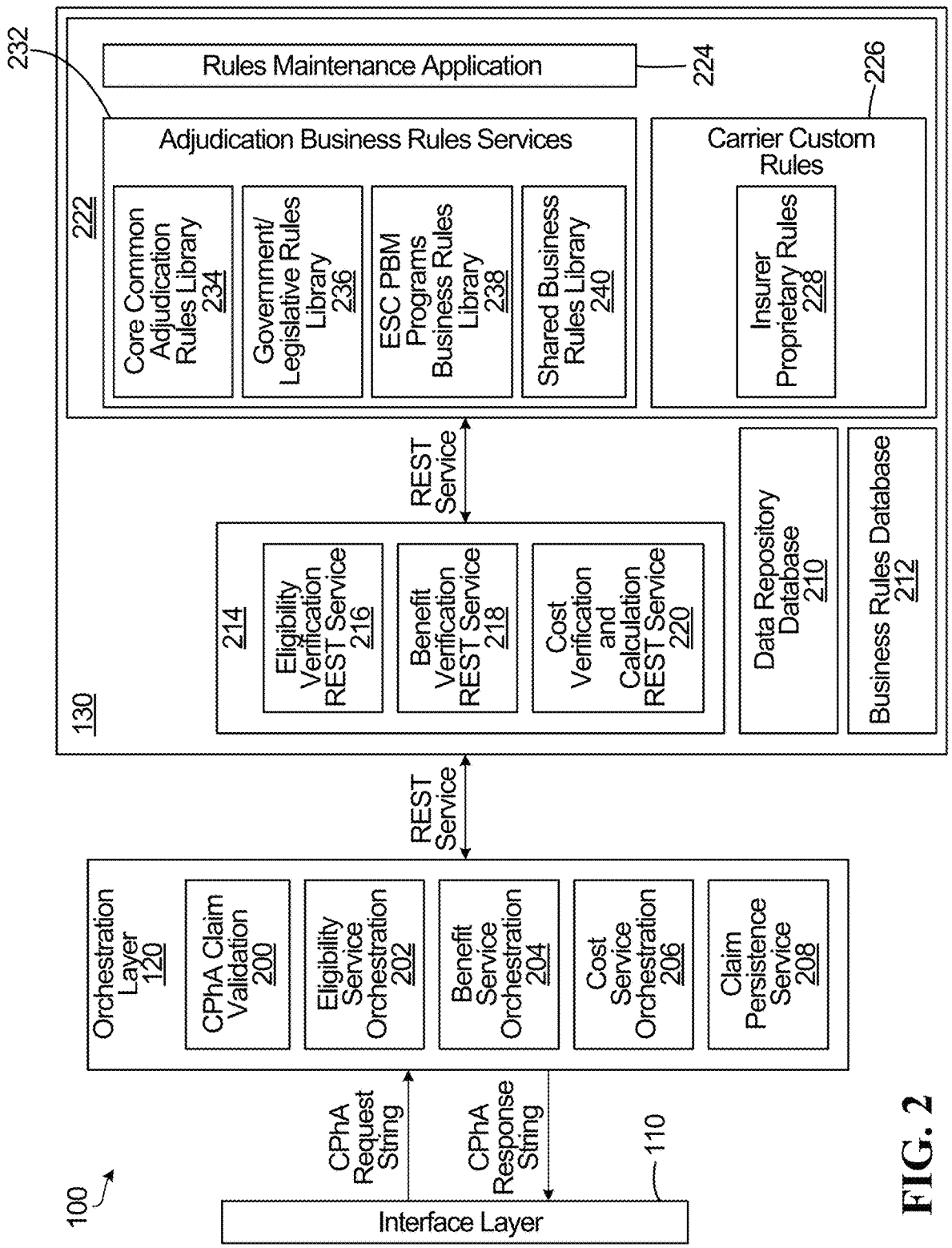
FIG. 2 shows a more detailed diagram of the pharmacy adjudication system 100 of FIG. 1 including an interface layer 110, an orchestration layer 120 and a service and rules engine layer 130.
Figure 3:
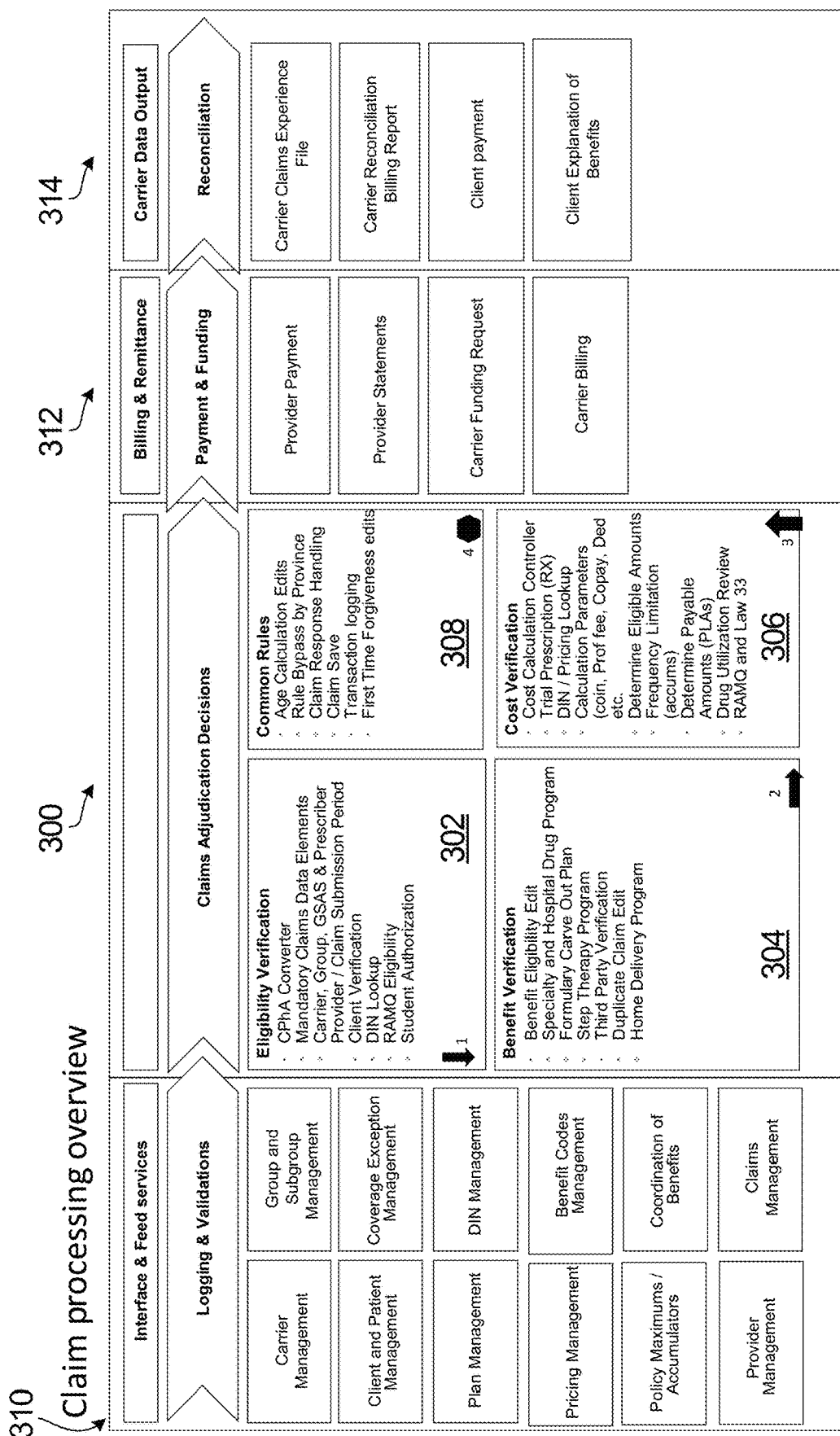
FIG. 3 shows an overview of an insurance claim process including mappings between specific service calls and corresponding subsets of rules in accordance with a specific embodiment of the invention.

A description of the components of the pharmacy adjudication system 100 and their functionality will now be presented in greater detail with reference to FIGS. 2 and 3. Embodiments of the various processes that may be implemented by the pharmacy adjudication system 100 to derive an adjudication decision corresponding to a healthcare insurance claim will be described with reference to FIGS. 4 to 7.

Pharmacy Adjudication System 100

As depicted, the pharmacy adjudication system 100 in accordance with an embodiment of the invention, comprises a set of layer namely an interface layer 110, an orchestration layer 120 and a service and rules engine layer 130. In some specific implementation, the orchestration layer 120 and a service and rules engine layer 130 may be built using a micro-service architecture.

Interface Layer 110

The interface layer 110 is programmed with the required functionality for interfacing the pharmacy adjudication system 100 with computer network 150 to enable the receipt and transmittal of information from/to external component connected to the data network 150. The interface layer 110 is itself in data communication with the orchestration layer 120 within the pharmacy adjudication system 100. The interface layer 110 is configured to receive a healthcare insurance claim originating from a POS device 160x via data network 150, the healthcare insurance claim including a plurality of information data elements specifying characteristics of the healthcare insurance claim.

It is appreciated that the healthcare insurance claim that is communicated to the interface layer 110 may comprise various information data elements specifying various characteristics of the health insurance claim including for example: name, date of birth, residence, drug prescription information, prescriber, issuing pharmacy and the likes.

The interface layer 110 is also configured for communicating the healthcare insurance claim in a suitable format for subsequent processing by the orchestration layer 120. In a non-limiting example, the healthcare insurance claim may be communicated to the orchestration layer 120 by the interface layer 110 using any suitable data format standard, such as but not limited to the Canadian Pharmacists Association Pharmacy Claim Standard (CPHA), the Canadian Dental Association format (CDANet), Extended Health claims format (HL7) and the likes.

After an adjudication decision corresponding to the healthcare insurance claim has been derived by the orchestration layer 120 and the service and rules engine layer 130 of the pharmacy adjudication system 100, as further described below, the interface layer 110 is configured to release the results for transmittal to the point of sale (POS) device 160x over data network 150, the results conveying an adjudication decision corresponding to the healthcare insurance claim.

Orchestration Layer 120

In a specific implementation, the orchestration layer 120 is programmed with the required functionality for communicating with the interface layer 110 to receive healthcare insurance claims and for releasing a corresponding adjudication decisions. The orchestration layer 120 is also programmed with the required functionality for communicating with the services and rules engine layer 130.

A role of the orchestration layer 120 is to control a flow of an adjudication process of an insurance claim by issuing various service calls to the services and rules engine layer 130. In a specific implementation, the orchestration layer 120 breaks down a health healthcare insurance claim into a sequence of individual service calls to the service and rules engine layer 130, where each of the service calls is for generating a corresponding partial decision result. The orchestration layer 120 is configured for processing the information data elements in the healthcare insurance claim received from the interface layer to generate a sequence of service calls for transmittal to the service and rules engine layer 130 to derive a sequence of partial decision results. The orchestration layer 120 is programmed for processing the sequence of partial decision results generated by the service and rules engine layer 130 in response to the generated sequence of service calls to derive the adjudication decision corresponding to the healthcare insurance claim. In some implementations, all partial decision results are first derived before the processing of the partial decision results is performed to derive the adjudication decision. Alternatively, the partial decision results may be processed sequentially, as they are available, to incrementally derive the adjudication decision. An advantage of processing the partial decision results sequentially is that in situations where not all partial decision results are necessary to arrive at a decision, some of the service calls can be foregone. Once derived, the adjudication decision is forward to the interface layer 110 for transmittal to the point of sale (POS) device 160x.

As mentioned above, the orchestration layer 120 breaks down a health healthcare insurance claim into a sequence of individual service calls to the service and rules engine layer 130. In practical implementations, the sequence of individual service calls will include two or more services calls and the break down may be done in different manners so as to simplify the processing of the healthcare insurance claims. In some specific non-limiting examples of implementation, the breakdown into specific service calls may be performed in a manner that allows results of at least some of the service call to be sufficient to come to an adjudication decision corresponding to the healthcare insurance claim without the need to performed additional service calls. Alternatively, or in addition, the breakdown into specific service calls may be performed to allow the result of at least some of the service call to be used by subsequent services calls to accelerate the processing of the subsequent service call.

In the specific pharmacy adjudication system 100 depicted in FIG. 2, the orchestration layer 120 is shown as breaking down the processing of a health healthcare insurance claim into a sequence of five (5) distinct service calls namely: a claim validation service call 200, an eligibility service call 202, a benefit service call 204, a cost service call 206 and a claim persistence service call 208. More specifically, in one non-limiting example, upon processing the information data elements contained in the healthcare insurance claim, the orchestration layer 120 generates a first service call related to claim validation service call 200, a second service call related to the eligibility service call 202, a third service call related to the benefit service call 204, a fourth service call related to the cost service call 206 and a fifth service call related to the claim persistence service call 208. It is to be appreciated that fewer or additional, including different, service calls may be used in alternative implementations. In some implementations, at least some of the service calls are associated with a set of parameters from the healthcare insurance claim. In the context of insurance claims, it is also to be appreciated that the service calls may be customized for a particular insurance carrier.

Optionally, for one of more of the service calls 200 202 204 206 208, the orchestration layer 120 may be configured to provide different versions. This may allow for example to have different version of a service call apply to different clients. In a non-limiting example, different insurance companies may have different benefit requirement and so different versions of the service call 204 may be provided and selection by the orchestration layer 120 depending on the identity of the insurance company.

According to this specific implementation, the claim validation service call 200 aims to determine whether the information data elements contained in the healthcare insurance claim are sufficiently complete, and that all information has been provided, to allow the healthcare insurance claim to be adjudicated. Examples of the type of processing that may be performed include, without being limited to, that the patient information, insurance plan information and healthcare treatment information (such as for example drug prescription information) have been provided as part of the healthcare insurance claim. Other examples may include, without being limited to verifying that:
- the insurance claim is well formed (e.g. adheres to CPHA standard);
- that all mandatory fields are present;
- that the fields are formatted correctly;
- that the date and time fields are valid.

The partial decision result of the claim validation service call 200 may convey if the insurance claim passed the validation rules or if it failed and why. As will be described later on, in a specific implementation this processing will performed by the services and rules layer 130 (described later below) by implementing rules such as, without being limited to:
- CPhA Converter;
- Mandatory Data Elements;
- Data Format Validation.

Still according to this specific implementation, the eligibility service call 202 aims to determine whether the healthcare insurance claim is eligible for a benefit under the benefit plan that would apply to the healthcare insurance claim. Examples of the type of processing that may be performed include, without being limited to, verifying whether the drug prescription information is part of a list of drugs covered by a benefits program for the patient. The partial decision result of the eligibility service call 202 may convey if the claim passed the eligibility rules or if it failed and why. As will be described later on, in a specific implementation this processing will performed by the services and rules layer 130 (described later below) by implementing rules such as, without being limited to: Validate Incoming claim against CPhA standards;
- Carrier, Group, GSAS & Prescriber;
- Provider/Claim Submission Period;
- Client Verification;
- DIN Lookup;
- RAMQ Eligibility.

Still according to this specific implementation, the benefit service call 204 aims to determine if the health insurance claim is covered by the insurance policy and to determine a corresponding benefit coverage for a claimant. The partial decision result of the benefit service call 204 may return information conveying whether the insurance claim was successful in passing the benefit rules or, if it failed, a reason why. As will be described later on, in a specific implementation this processing will be performed by the services and rules layer 130 (described later below) by implementing rules such as, without being limited to:
- Benefit Eligibility Edit;
- Specialty and Hospital Drug Program;
- Formulary Carve Out Plan;
- Step Therapy Program;
- Duplicate Claim Edit;
- Home Delivery Program.

Still according to this specific implementation, the cost service call 206 aims to determine the amount that will be paid and how it will be paid in connection with the healthcare insurance claim. The partial result of the cost service call 206 may return information conveying whether an amount will be paid for the insurance claim and an entity that is paying the amount. Examples of the type of processing that may be performed include, without being limited to, calculating the deductible amount and percentage of coverage for the specific drug conveyed by the drug prescription information. As will be described later on, in a specific implementation this processing will performed by the services and rules layer 130 (described later below) by implementing rules such as, without being limited to:
- Cost Calculation Controller;
- Trial Prescription (RX);
- DIN/Pricing Lookup;
- Calculation Parameters;
- Determine Eligible Amounts;
- Policy Limitations;
- Determine Payable Amounts;
- Drug Utilization Review;
- RAMQ and Law 33.

Still according to this specific implementation, the claim persistence service call 208 aims to save/maintain a record including all the health insurance claim information and the adjudication result obtained in the data repository 210 once the health insurance claim has been processed. In this specific implementation, the partial decision result of the claim persistence service call 208 may for example convey that the record was successfully updated.

With reference to service calls 200 202 204 206 and 208, it is to be appreciated that not all services calls need to be performed in order to derive the adjudication decision for the healthcare insurance claim. For example, if the service of the claim validation service call 200 indicates that the healthcare insurance claim is incomplete and cannot be processed, service calls 202 204 206 and 208 can be skipped and the result of the adjudication process may be derived based on the partial decision result of the claim validation service call 200 alone. In this case, the adjudication decision would convey that the healthcare insurance claim was refused. In another example, of the service of the claim validation service call 200 indicated that the healthcare insurance claim was complete but the eligibility service call 202 result indicated that the specific drug in the healthcare insurance claim was not covered by the plan, the service calls 204 206 and 208 can be skipped and the result of the adjudication process may be derived based on the partial decision results of the claim validation service call 200 and the eligibility service call 202. In this case, the adjudication decision would also convey that the healthcare insurance claim was refused. Additional examples and explanations will be presented later on in the present document to illustrate the functioning of the orchestration layer 120.

The person skilled in the art will also appreciate that while the orchestration layer 120 has been shown to include the five (5) specific service calls shown in FIG. 2, alternative embodiments may omit some service calls altogether. Alternatively still, other embodiments may break down the processing of a health healthcare insurance claim into completely different services call each having different aims/objectives than those presented here. This it is to be understand that the specific example of a sequence of service calls described has been shown for the purpose of illustration so assist the reader but that alternatives are possible and will become apparent to the person skilled in the art in view of the present description.

Once partial decision results have been obtained, an adjudication decision corresponding to the healthcare insurance claim is derived by processing the partial decision results. Various rules, including heuristic rules, may be used by the orchestration layer 120 in processing partial decision results to derive an adjudication decision. The specific rules used to arrive to an adjudication decision may vary between implementations, are not critical to the invention and will become apparent to the person skilled in the art in light of the knowledge in the art and the present description. As such, such specific rules will not be described in further detail in the present document.

As mentioned above, the sequence of service calls made by the orchestration layer 120 results in a sequence of corresponding partial decision results, with each specific partial decision result corresponding to a specific service call made to the service and rules engine layer 130. The structure and processes implemented by the service and rules engine layer 130 are described in the following section.

Service and Rules Engine Layer 130

The service and rules engine layer 130 is in communication with the orchestration layer 120 described above. The service and rules engine layer 130 is configured for receiving from the orchestration layer 120 a sequence of service calls identifying respective sets of parameters on which each of the service calls is to be applied. For each service call, the service and rules engine layer 130 is configured for deriving a partial decision result at least in part by processing the set of parameters identified by the service call according to one or more decision rules from the rules repository, the one or more decision rules corresponding to the service call and being a subset of decisions rules in the rules repository. Example of specific processes for deriving a specific partial decision result for each one of the service call issued by the orchestration layer will be further described in connection with FIGS. 4-7.

The service and rules engine layer 130 make use of information stored in a data repository 210 and a rules repository in order to derive specific partial decision results, wherein the rules repository is shown in the example of FIG. 2 as being comprised of a business rules database 212 and a set of rules libraries 234 236 238 240 228 and 230. The data repository 210 and one or more components of the rules repository (i.e., one or more of the business rules database 212 and the set of rules libraries 234 236 238 240 228 and 230) may be integral parts of the service and rules engine layer 130 or, alternatively, may be separate components in communications with the service and rules engine layer 130 over a data network. Irrespective, the data repository 210 and one or more components of the rules repository may be stored on non-transitory computer readable media that can be accessed by one or more processors either locally or over a computer network. It will also be appreciated that, in some implementations, any rule queried within set of rules libraries 234 236 238 240 228 and 230 may be queried directly within the specific library or in the business rules database 212.

The data repository 210 stores health insurance information for a plurality of insured users. The specific contents of the data repository may vary between implementations and may also be dynamically adapted based on on-going insurance claim activities. In a specific example of implementation, the data repository 210 stores information including, but not limited to: identification information associated with insured users; lists of drugs covered by the prescription drug benefits programs; insurance claim history of the insured users; drug and drug pricing information; drug utilization review (DRU); prescriber information.

The rules repository stores a set of business decision rules for processing a healthcare insurance claim. Generally, each service call made to the service and rules engine layer 130 will correspond to a subset of the set of business decisions rules in the rules repository, wherein each subset will be comprised of one or more rules from the set of rules in the repository. In the example of FIG. 2, the rules repository is shown as being comprised of a business rules database 212 and a set of rules libraries 234 236 238 240 228 and 230. In the example depicted, the rules repository 212 includes:

A subset of rules for adjudication business rules services 232 such as for example:
- a Core Common Adjudication Rules Library 234 storing core adjudication rules;
- a Government/Legislative Rules Library 236 storing legislative requirements, such as but not limited to Ontario Health Insurance Plan (OHIP) and the like;
- a ESC PBM programs Business Rules library 238 storing rules pertaining to insurance programs developed by the specific insurance carrier and made available to all insurance carriers; and/or
- a Shared Business Rules library 240 storing rules available to all insurance carriers;

A subset of rules for carrier custom rules 226 developed for a specific carrier and available for use only by that carrier such as, for example:
- Proprietary rules pertaining to insurer insurance programs 228;

The business rules database 212 depicted may store other rules than those in libraries 234 236 238 240 228 and 230 and that may be useful in deriving an adjudication decision in connection with a healthcare insurance claim. In some non-limiting examples of implementation, the business rules database 212 may also provide a mapping between a specific service call and one or more corresponding rules, which allows the orchestration of rule execution to be externalized in the rules database.

It is to be appreciated that the types of rules in the rules repository may vary between implementations and the examples shown have been presented for the purpose of illustration. For example, different rules may be called upon based on whether the healthcare insurance claim is a claim for a prescription or a dental claim.

The derivation of a partial decision result by the service and rules engine layer 130 corresponding to a specific service call issued by the orchestration layer 120 may be conditioned at least in part on a number of factors such as, but without being limited to:

(i) a subset of the set of parameters characterizing the healthcare insurance claim; and/or
(ii) a subset of the rules from the rules repository, including for example rules in the business rules database 212 and/or rules in any of in libraries 234 236 238 240 228 and 230; and/or
(iii) a subset of data from the data repository 210.

In specific implementations, the service and rules engine layer 130 is configured for processing an incoming service call to identify a subset of rules in the rules repository to be used to derive a partial decision result corresponding to that service call. In a specific implementation, the service modules in the service sublayer 214 are configured to identify in one or more of the business rules database 212 as well as other rules libraries 234 236 238 240 228 and 230 to identify as subset of rules for a specific service call. Similarly, the service and rules engine layer 130 is configured for processing an incoming service call to identify a subset of data from the data repository 210 corresponding to that service call.

In some specific implementations, of the type depicted in FIG. 2, the service and rules engine layer 130 comprises a service sublayer 214 in communication with a rules engine sublayer 222. In In some specific implementations, each of service sublayer 214 and the rules engine sublayer 222 may be built using a micro-service architecture.

The service sublayer 214 is configured to coordinate a series of workflows with the rules engine sublayer 222 in order to process a service call received from the orchestration layer 120. More specific, the service sublayer 214 is configured to receive and process the various service calls generated by the orchestration layer 120, specifically any one of the relevant orchestration service calls 200, 202, 204, 206 and 208. In the specific implementation depicted, the service sublayer 214 is data communication with the rules engine sublayer 222, and may be in communication with the data repository 210. Communication between the service sublayer 214 and the rules engine sublayer 222 as well the communications between the orchestration layer 120 and the service sublayer 214 may be done using any suitable service, such as but not limited to the Representational State Transfer (REST) service. The rules engine sublayer 222 is configured for receiving requests from the service sublayer 214 to apply a specific rule to specific parameters in order to generate a corresponding result. In practical implementations, the individual rules implemented by the rules engine sublayer 222 are preferably configured to be substantially independent of each other in order to reduce rule complexity and their management. In some specific implementations, the rules engine sublayer 222 may be implemented in whole or in part using commercial off-the-shelf business rules systems such as for example, the FICO® Decision management suite, IBM Operational Decision Manager, RedHat Decision Manager or any open source BRMS. Other suitable off-the-shelf business rules systems as well as custom built business rules systems may also be used in alternative implementations. In this context, the service sublayer 214 can be considered to provide an interface between the orchestration layer 120 and the rules engine sublayer 222.

In the example depicted, the service sublayer 214 implements a number of service modules including for example but without being limited to: an eligibility verification REST service module 216, a benefit verification REST service module 218 and a cost verification and calculation REST service module 220. Each one of these specific REST service modules is configured to receive and process the relevant service call originating from the orchestration layer 120 (for example the eligibility verification REST service module 216 is configured for receiving and processing an eligibility service call 202 generated by the eligibility service orchestration layer 120). Each of the service modules is configured for identifying and launching one or more rules corresponding to a received service call to the rules engine sublayer 222. In other words, the service modules in the service layer 214 may be configured to identify within the rules repository a specific subset of rules that is needed to derive a partial decision result for the specific service call. For example, in the context of a service call regarding eligibility verification, the eligibility verification REST service 216 identifies a specific subset of rules within the rules repository that is relevant to derive of a partial decision result regarding eligibility verification.

With reference to FIG. 3, non-limiting examples of mappings between subsets of rules 302 304 306 and 308 and various services calls are shown. The mappings may be stored in the business rules database 212 (shown in FIG. 2) or, alternatively, may be stored the service sublayer 214. In the example of FIG. 3, a service call regarding eligibility verification will call upon a corresponding subset of rules 302 including, for example but without being limited to:
  a CPhA conversion (to convert the CPhA string format in a format usable by the service and rules layer 130);
  mandatory claim elements (to ensure that all the information that is required to process the healthcare insurance claim is present—this will relate at least in part to the set of parameters representative of the healthcare insurance claim);
  the identity of the carrier, prescriber etc., the submission period for the claim;
  a drug identification number (DIN) lookup;
  RAMQ eligibility; and/or
  student authorization and the likes.

In another example, a service call regarding benefit verification will call upon a corresponding subset of rules 304 including, for example:
  benefit eligibility edits;
  specialty and hospital drug programs;
  formulary carve out plans;
  step therapy programs;
  third party verification;
  duplicate claims; and/or
  home delivery programs and the likes.

In yet another non-limiting example, a service call regarding cost verification will call upon a corresponding subset of rules 306 including, for example but without being limited to:
  rules regarding cost calculations;
  trial prescriptions;
  pricing lookup;
  calculation parameters;
  eligible amounts;
  frequency limitations; and/or
  payable amounts and the likes.

In some embodiments, the service sublayer 214 is configured to query a data repository 210. In particular, it will be appreciated that, in order to derive a partial decision result regarding a service call received from the orchestration layer 120, the service and rules engine layer 130 may need to consider data that is not present in the healthcare insurance claim itself, and accordingly in the set of parameters representative of the healthcare insurance claim. For example, in the context of a prescription for a drug that has already been prescribed in the past, the rule regarding frequency limitation requires data regarding the date of a new prescription for the drug (information that is present in the healthcare insurance claim) as well as the data regarding the date of a previous prescription (information that is not present in the healthcare insurance claim). As such, the data repository 210 may comprise information related to a plurality of insured individuals and specifically regarding the health insurance claim history of the individuals. The service sublayer is therefore configured, for a specific service call, to identify a specific subset of rules required to derive a partial decision result for the specific service call. On the basis of the identified subset of rules, the service sublayer 214 is also configured to identify a specific subset of data within the data repository 210 that is required to execute the identified subset of rules and derive a partial decision result for the specific service call.

Specific Example of Adjudication Process

A specific example of a process for performing an adjudication service in connection with a healthcare insurance claim originating from a point of sale (POS) device and that may be implemented by the pharmacy adjudication system depicted in FIGS. 1 and 2 will now be described with reference to FIGS. 4 to 7.

As depicted, at step 400, a healthcare insurance claim originating from a POS device 160x is received at the interface layer 110 of the pharmacy adjudication system 100.

At step 402, the various data elements comprised within the healthcare insurance claim are processed, notably by the orchestration layer 120, to generate a sequence of service calls to the service and rules engine layer 130. The service and rules engine layer 130 processes the services calls in the sequence of service calls to derive a corresponding sequence of partial decision results, which are returned to the orchestration layer 120. In one illustrative example:
- a first service call that relates to eligibility verification may be generated and a partial decision result relating to such eligibility verification may be derived at step 402.;
- a second service call that relates to benefit verification may also be generated and a partial decision result relating to such benefit verification may also be derived at step 402;
- a third service call that relates to cost verification may also be generated and a partial decision result relating to such cost verification may also be derived at step 402.

Fewer or additional service calls made be generated in alternative implementations.

At step 404, the sequence of partial decision results obtained are processed by the orchestration layer 120 to derive an adjudication decision corresponding to the healthcare insurance claim received at step 400. Continuing the specific example presented above with reference to step 402, the sequence of partial decision results relating to eligibility verification (first), benefit verification (second) and cost verification (third) may be processed in that specific sequence to derive an adjudication decision corresponding to the healthcare insurance claim received at step 400. It is to be appreciated that not all partial decision results in the sequence of partial decision results may need to be processed to arrive at the adjudication decision. For example, assuming that in one non-limiting example the partial decision result relating to eligibility verification is negative (i.e., the partial decision result is that the healthcare insurance claim is not eligible), then further processing of the second partial decision result relating to benefit verification and the third partial decision result relating to cost verification are not necessary. More specifically, since the first partial decision result relating to eligibility verification is negative, the adjudication decision will necessarily be negative and the subsequent partial decision results will have no impact of the adjudication decision and may therefore be by-passed.

At step 406, the adjudication decision is transmitted in the form of results via the data network 150 to the POS device 160x.

Figure 4:
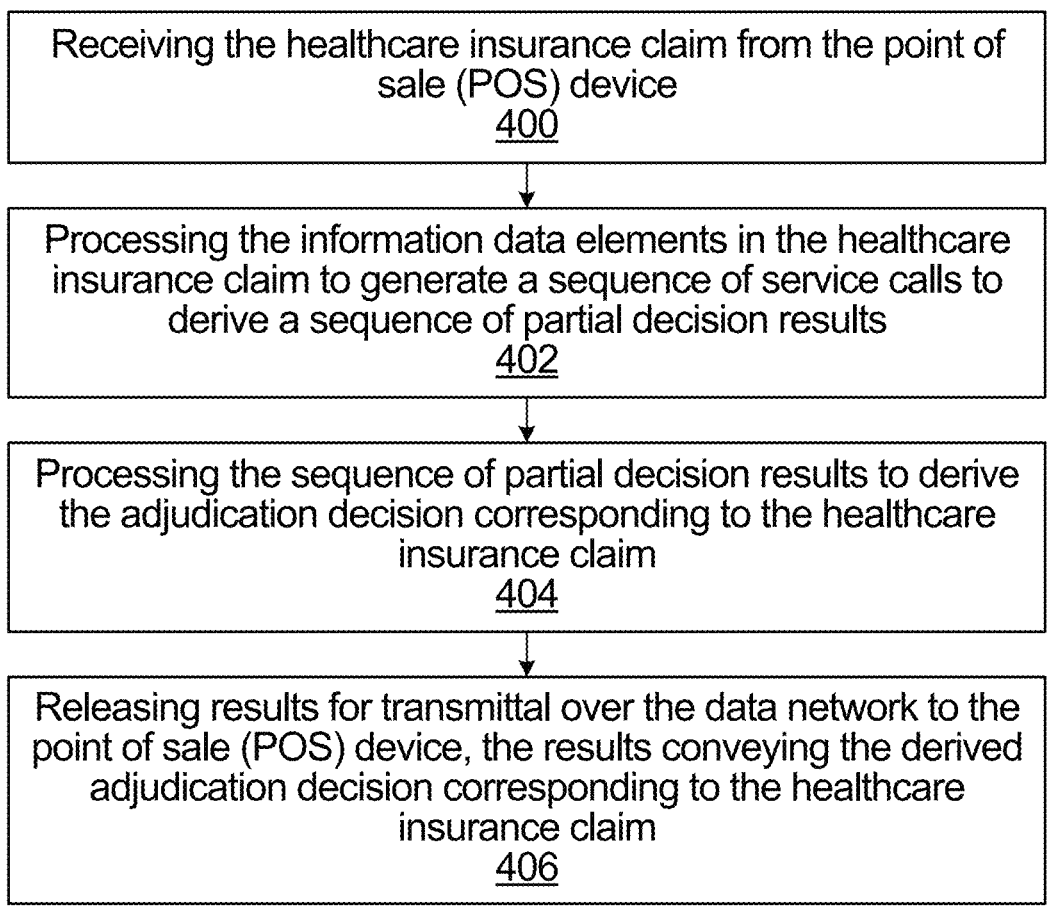
FIG. 4 shows a process for deriving an adjudication decision corresponding to a healthcare insurance claim using the pharmacy adjudication system of 100 shown in FIGS. 1 and 2 in accordance with specific embodiment of the invention, including generating a sequence of service calls for deriving a corresponding sequence of partial decision results.
Figure 5:
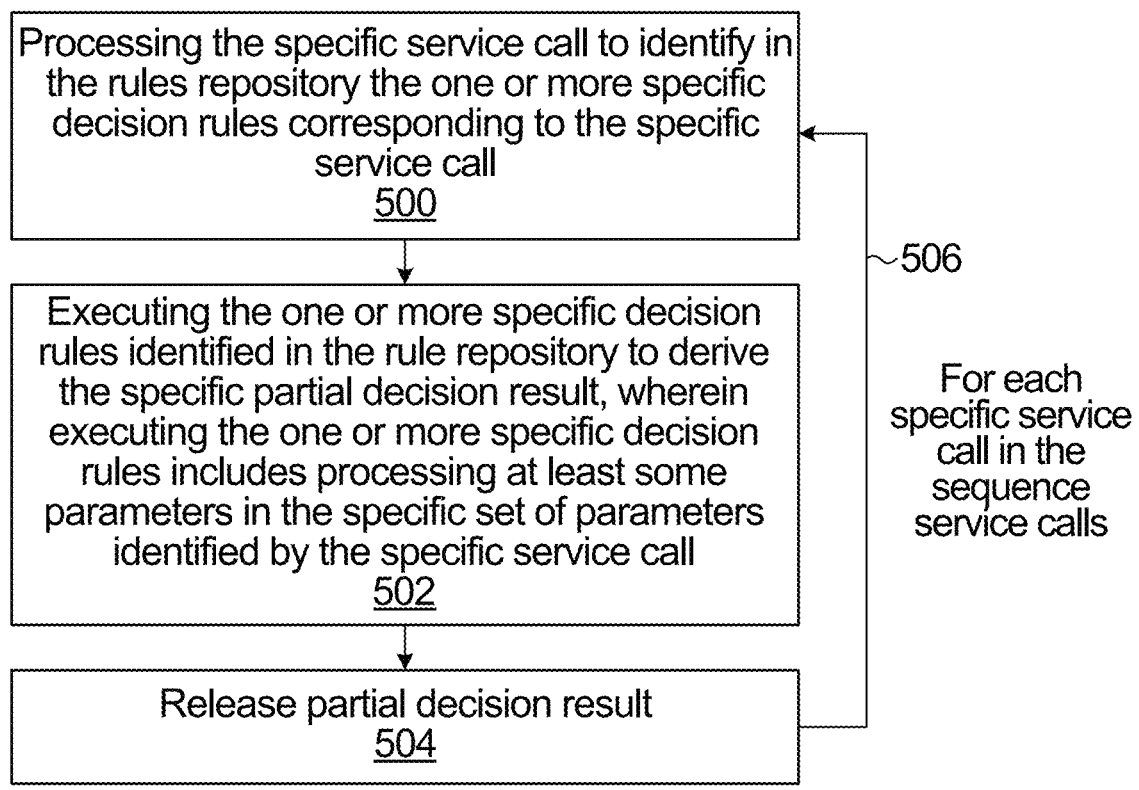
FIG. 5 shows a process corresponding to the processing of the sequence of service call of FIG. 4 for deriving a sequence of partial decision results in accordance with a specific embodiment.

FIG. 5 shows with greater specificity the processing that may be performed at step 402 of FIG. 4 to deriving a sequence of partial decision results. In a specific implementation, the process depicted in FIG. 5 would be implemented by the service and rules layer 130. More specifically, for each service call in the sequence of service calls, at step 500, the service call is processed, notably by the service and rules engine layer 130, to identify in the rules repository (shown in FIG. 2 as being comprised of a business rules database 212 and a set of rules libraries 234 236 238 240 228 and 230) one or more specific rules that correspond to the service call and therefore may be needed to derive the corresponding partial decision result. The rules one or more specific rules that correspond to the service call may be identified in different manner, such as for example by providing a mapping between service calls and subsets of rules of the type shown in the process depicted in FIG. 3. At step 502, the one or more specific decision rules identified at step 500 are executed to derive the specific partial decision result. It is appreciated that, at step 502, the execution of the one or more specific decision rules may include processing at least some parameters in a set of parameters identified in the specific service call. The set of parameters identified in the specific service call convey characteristics of the healthcare insurance claim.

At step 504 the partial decision result corresponding to the service call is released and returned to the orchestration layer 120 (shown in FIG. 2). If there are remaining service calls to be performed (as may be determined the orchestration layer 120) the process returns to step 500 and the other service call is processed. If all required service calls have been processed, the process ends after step 504 and step 402 (shown in FIG. 4) is complete and the process proceeds to step 404.

Figure 6:
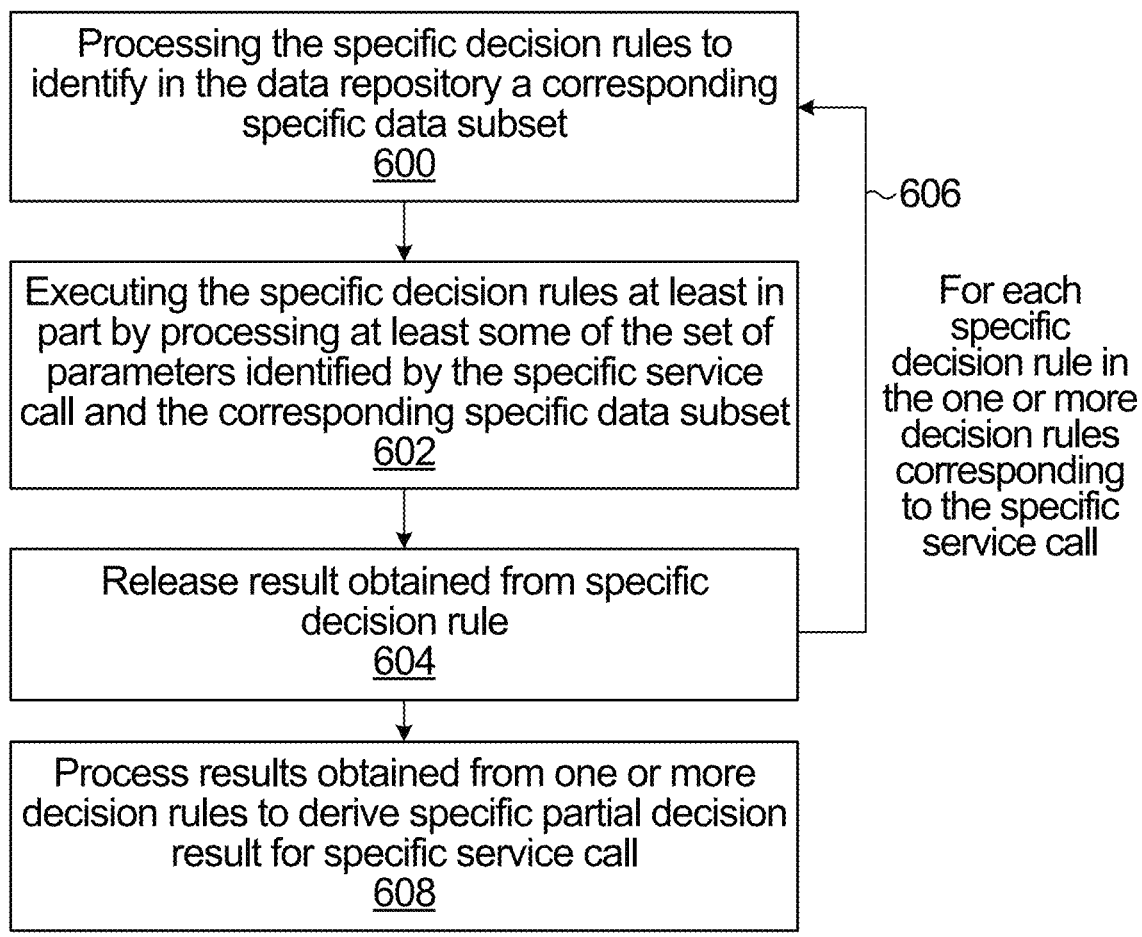
FIG. 6: shows a process for deriving a specific partial decision result corresponding to a specific service call made to the service and rules engine layer 130 shown in FIGS. 1 and 2 in accordance with a specific embodiment.

FIG. 6 shows with greater specificity the processing that may be performed at step 502 of FIG. 5 to derive a specific partial decision result corresponding to a specific service call. In a specific implementation, the process depicted in FIG. 6 would be implemented by the service and rules layer 130. More specifically, for each specific decision rule in the one or more decision rules identified at step 500 as corresponding to the specific service call, at step 600, the specific decision rules is processed to identify in data repository 210 (shown in FIG. 2) a specific data subset required for the execution of the specific decision rule. At step 602, the specific decision rules is executed using information in the rules repository at least in part by processing parameters identified by the specific service call and the data subset derived at step 600. At step 604 the result of the specific rule is released. If there are remaining rules identified at step 500 as corresponding to the specific service call that have not yet been processed, the process returns to step 600 and the next unprocessed rule considered. If all rules identified at step 500 as corresponding to the specific service call have been processed, after step 604 the process proceeds to step 608. At step 608, the results obtained by executing each of the specific rules corresponding to the specific service call are processed to derive the partial decision result for the specific service call. After step 608, step 502 (of FIG. 5) is considered complete and the process proceeds to step 504.

Communication Exchanges within the Pharmacy Adjudication System 100

Figure 7:
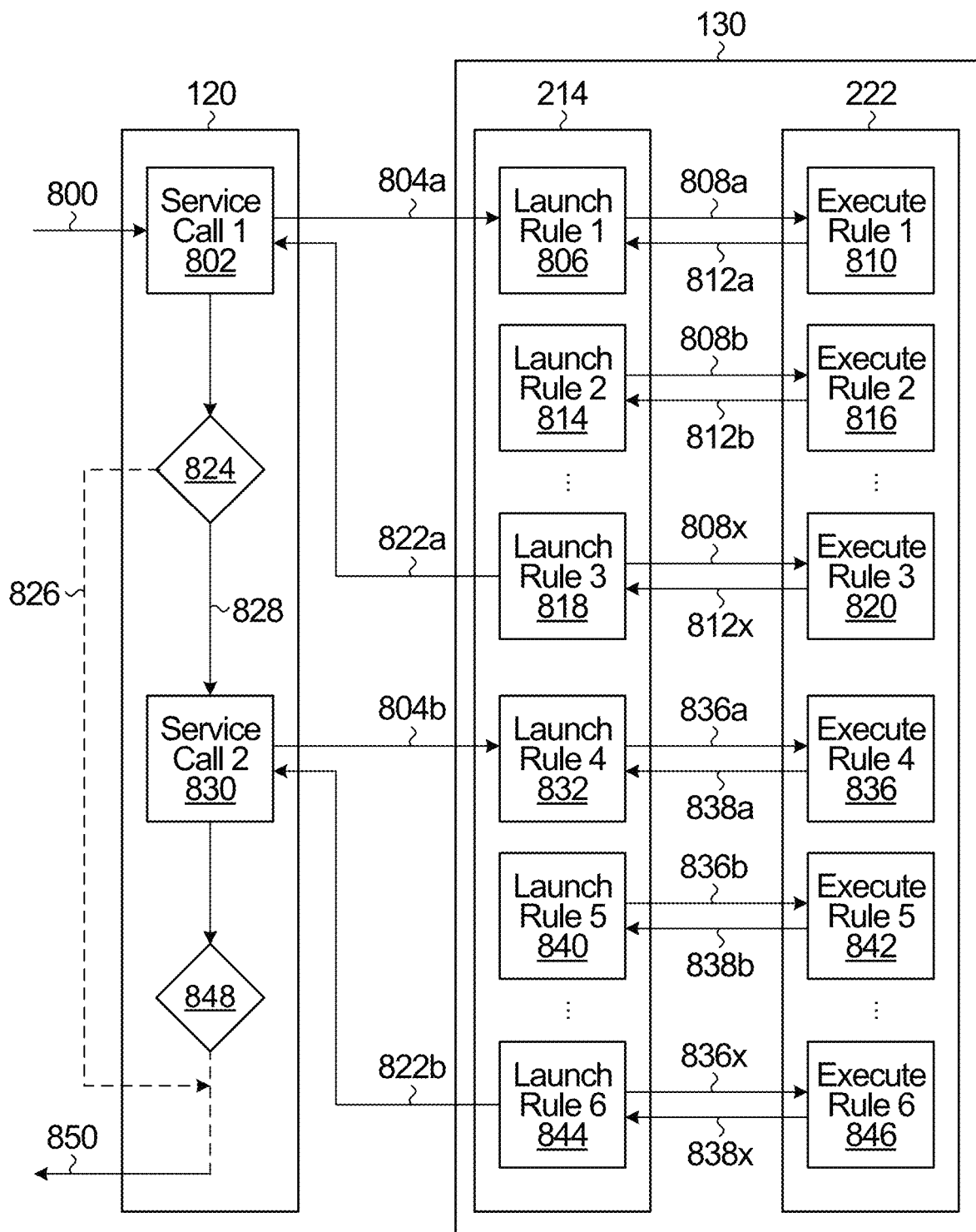
FIG. 7 shows a communication diagram illustrating communication flows between the orchestration layer 120 and the service and rules engine layer 130 of the pharmacy adjudication system 100 shown in FIG. 2 in accordance with a specific implementation.

A very specific example of communication exchanges between the orchestration layer 120 and service and rules layer 130 of the pharmacy adjudication system 100 for deriving the sequence of partial decision results and the adjudication decision will now be described with reference to FIG. 7.

Via transmission 800, the orchestration layer 120 receives a communication from the interface layer 110 (shown in FIGS. 1 and 2) corresponding to the healthcare insurance claim and including a plurality of information elements. The orchestration layer 120 then processes the plurality of data elements and derives a sequence of individual service calls, starting with a first service call 802. Via communication 804a, the orchestration layer 120 then transmits the first service call 802 to the service and rules engine 130 for processing.

In the specific example shown, the service sublayer 214 executes a plurality of rules 806 814 818 corresponding to the first service call to derive a partial decision result corresponding to the first service call 802. In this non-limiting embodiment, the first service call requires the launching and execution of three rules 806 814 818 to derive the partial decision result related to the first service call. It is however to be appreciated that this is only intended as an illustration and that any suitable number of rules may be launched and executed for any particular service call. The service sublayer 214 first creates a command to launch the first rule 806 and transmits it via communication 808a to the rules engine sublayer 222 to execute the first rule 810. The rules engine layer 222 then communicates the result of the execution of the first rule to the service sublayer 214 via communication 812a. The service sublayer 214 then reiterates this process for the second rule 814 and third rules 818 in this non-limiting embodiment by launching them via communications 808b and 808x. Once the result of the execution of the second rule 814 and third rule 818 have been communicated to the service sublayer 214 by the rules engine sublayer 222 via communications 812b and 812x, a partial decision result is derived for the first service call and communicated to the orchestration layer 120 via communication 822a.

In this specific implementation, the orchestration layer 120 makes a determination at step 824 as to whether the process should continue with a second service call at step 830 via communication 828, or whether the partial decision result obtained via communication 822a is sufficient to derive an adjudication decision corresponding to the healthcare insurance claim received via communication 8000. In the former case, the process described above in connection with the first service call is repeated for the second service call 830 until a partial decision result regarding the second service call in the sequence of service calls being generated by the orchestration layer 120 in response to the transmission 800.

More specifically, with reference to the second service call 830, via communication 804b, the orchestration layer 120 transmits the second service call 830 to the service and rules engine 130 for processing. In the specific example shown, the service sublayer 214 executes a plurality of rules 832 840 844 corresponding to the second service call to derive a partial decision result corresponding to the second service call 830. The service sublayer 214 first creates a command to launch rule 832 and transmits it via communication 836a to the rules engine sublayer 222 to execute the first rule 832. The rules engine layer 222 then communicates the result of the execution of the rule 832 to the service sublayer 214 via communication 838a.

The service sublayer 214 then reiterates this process for the other rules 840 844 by launching them via communications 836b and 836x. Once the result of the execution of these other rules 840 844 have been communicated to the service sublayer 214 by the rules engine sublayer 222 via communications 838b and 838x, a partial decision result is derived for the second service call and communicated to the orchestration layer 120 via communication 822b.

The process described above in connection with the first and second service calls are repeated for any other service call being generated by the orchestration layer 120 in response to the transmission 800.

The adjudication decision may then be derived by the orchestration layer 120 and communicated to the interface layer 110 via communication 850.

Practical Example of Implementation for Electronic Pharmacy Adjudication System 100

Those skilled in the art should appreciate that in some non-limiting embodiments, all or part of the functionality previously described herein with respect to the electronic pharmacy adjudication system 100 for performing an adjudication service in connection with a healthcare insurance claim as described throughout this specification may be implemented as software including computer program instructions for execution by one or more processors. The computer program instructions can be tangibly stored on one or more non-transitory computer readable storage media, or the instructions can be tangibly stored remotely but transmittable to the one or more processors via a modem or other interface device (e.g., a communications adapter) connected to a computer network over a transmission medium. The transmission medium may be either a tangible medium (e.g., optical or analog communications lines) or a medium implemented using wireless techniques (e.g., microwave, infrared or other transmission schemes).

Those skilled in the art should further appreciate that the program instructions may be written in any of a number of suitable programming languages for use with many computer architectures or operating systems.

Figure 8:
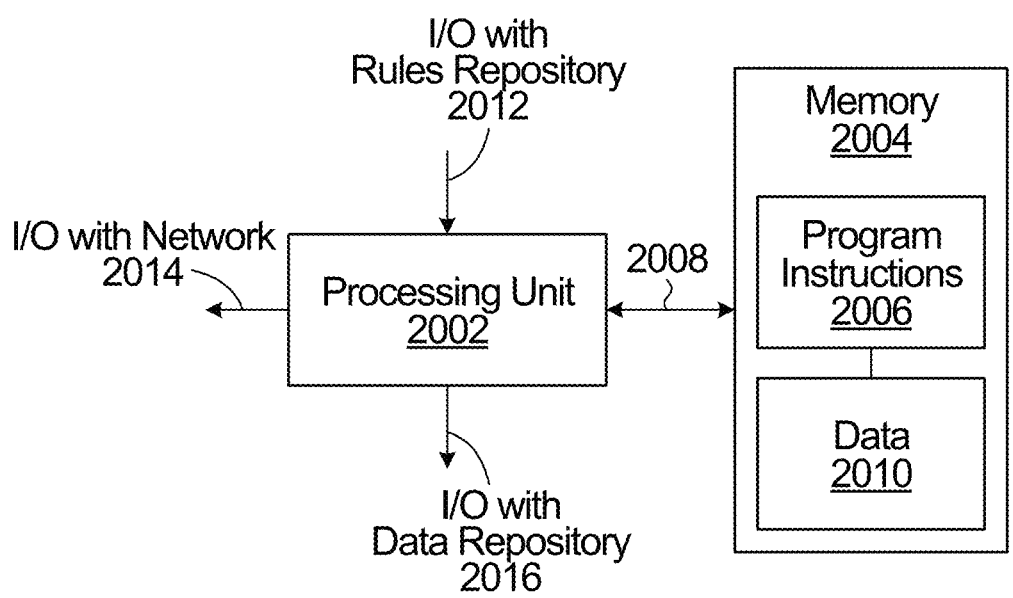
FIG. 8 shows a computing apparatus for implementing the pharmacy adjudication system 100 shown in FIGS. 1 and 2 in accordance with a specific implementation.

In a non-limiting example, some or all the functionality of the electronic pharmacy adjudication system 100 may be implemented on a suitable computing device 2000, of the type depicted in FIG. 8. Such a computing device 2000 typically includes a processing unit 2002 and a memory 2004 that is connected by a communication bus 2008. The memory 2004 includes program instructions 2006 and data 2010. The processing unit 2002 is adapted to process the data 2010 and the program instructions 2006 in order to implement the functionality described and depicted in the drawings with reference to the electronic pharmacy adjudication system 100. The microprocessor 2000 may also comprise one or more input/output (I/O) interfaces 2014 2012 2016 for receiving or sending data elements to external modules. In the specific example depicted in FIG. 8, the computing device 2000 is shown with three I/O interfaces, namely:

a first I/O interface 2014 for establishing communications with POS devices through a data network (such as POS devices 160a-x and data network 150 shown in FIG. 1);

a second I/O interface 2016 for establishing communications either directly or through a data network with a data repository data base (such as data repository database 210 shown in FIG. 2);

a third I/O interface 2012 for establishing communications either directly or through a data network with a rules repository (shown in FIG. 2 as being comprised of a business rules database 212 and a set of rules libraries 234 236 238 240 228 and 230).

It is to be appreciated that while the computing device 2000 has been shown with a specific structure, many other variations are possible and will become apparent to the person skilled in the art in view of the present description. For example, while the computing device 2000 has been shown with I/O interfaces 2012 and 2016 for communications either directly or through a data network with an external data repository database and an external rules repository, it is to be appreciated that either one or both the external data repository database 210 and the external rules repository may be part of the computing device 2000, for example they may be part of the data 2010 in memory 2004. In such cases either one, or both, the I/O interfaces 2012 and 2016 may be omitted in such implementations. As another example, the person skilled in the art will appreciated in view of the present description that, in some embodiments, the electronic pharmacy adjudication system 100 depicted in FIG. 1 may be implemented as a distributed system where the interface layer 110, the orchestration layer 120 and/or the service and rules engine layer 130 may each be implemented by one or more machines interconnected with one another over a communications network.

Thus, although the present invention has been described with reference to specific features and embodiments thereof, various modifications and combinations can be made thereto. The description and drawings are, accordingly, to be regarded simply as an illustration of some embodiments of the invention as defined by the appended claims, and are contemplated to cover any and all modifications, variations, combinations or equivalents that fall within the scope of the present invention. Therefore, although the present invention and its advantages have been described in detail, various changes, substitutions and alterations can be made herein without departing from the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed, that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

Note that titles or subtitles may be used throughout the present disclosure for convenience of a reader, but in no way these should limit the scope of the invention. Moreover, certain theories may be proposed and disclosed herein; however, in no way they, whether they are right or wrong, should limit the scope of the invention so long as the invention is practiced according to the present disclosure without regard for any specific theory or scheme of action.

All references cited throughout the specification are hereby incorporated by reference in their entirety for all purposes.

It will be understood by those of skill in the art that throughout the present specification, the term "a" used before a term encompasses embodiments containing one or more to what the term refers. It will also be understood by those of skill in the art that throughout the present specification, the term "comprising", which is synonymous with "including," "containing," or "characterized by," is inclusive or open-ended and does not exclude additional, un-recited elements or method steps.

Unless otherwise defined, all technical and scientific terms used herein have the same meaning as commonly understood by one of ordinary skill in the art to which this invention pertains. In the case of conflict, the present document, including definitions will control.

As used in the present disclosure, the terms "around", "about" or "approximately" shall generally mean within the error margin generally accepted in the art. Hence, numerical quantities given herein generally include such error margin such that the terms "around", "about" or "approximately" can be inferred if not expressly stated.

Although various embodiments of the disclosure have been described and illustrated, it will be apparent to those skilled in the art in light of the present description that numerous modifications and variations can be made. The scope of the invention is defined more specifically in the appended claims.

The invention claimed is:

1. An electronic pharmacy adjudication system for performing an adjudication service in connection with healthcare insurance claims originating from a plurality of point of sale (POS) devices, each of the healthcare insurance claims including a plurality of information data elements specifying characteristics of the healthcare insurance claim, the electronic pharmacy adjudication system comprising:
   one or more processors; and
   a non-transitory computer readable memory storing computer program instructions, the computer program instructions when executed by the one or more processors implementing:
   a) a service and rules engine layer configured for:
      i) receiving a service call identifying a set of parameters on which the service call is to be applied; and
      ii) deriving a partial decision result at least in part by processing the set of parameters identified by the service call according to one or more decision rules from a rules repository, the one or more decision rules corresponding to the service call and being a subset of decisions rules in the rules repository;
   b) an orchestration layer in communication with said service and rules engine layer, said orchestration layer being configured for:
      i) processing the information data elements in at least 20,000 of the healthcare insurance claims to generate a sequence of service calls for each of the at least 20,000 of the healthcare insurance claims and forwarding a first service call in the sequence of service calls to the service and rules engine layer to derive a first partial decision result corresponding to the first service call;
      ii) forwarding one or more subsequent service calls in the sequence of service calls to the service and rules engine layer to derive one or more subsequent partial decision results in a sequence of partial decision results when an adjudication decision corresponding to a respective one of the at least 20,000 of the healthcare insurance claims cannot be derived from a previous partial decision result in the sequence of partial decision results corresponding to a previous service call in the sequence of service calls;
      iii) processing the sequence of partial decision results generated by the service and rules engine layer in response to the generated sequence of service calls to incrementally derive the adjudication decision corresponding to each of the at least 20,000 of the healthcare insurance claims;
      iv) forwarding the derived adjudication decision corresponding to each of the at least 20,000 of the healthcare insurance claims to an interface layer for transmittal to a respective one of the point of sale (POS) devices via a data network.

2. The electronic pharmacy adjudication system of claim 1, wherein the service and rules engine layer is in communication with a data repository containing health insurance information for a plurality of insured users.

3. The electronic pharmacy adjudication system of claim 2, wherein the data repository contains lists of drugs covered by a prescription drug benefits programs for at least some of the plurality of insured users.

4. The electronic pharmacy adjudication system of claim 2, wherein the service and rules engine layer is configured for:
   a) processing the service call to identify in the data repository a data set for use by the service call;
   b) deriving the partial decision result at least in part by processing data in the identified data set and the set of parameters identified by the service call according to the one or more decision rules corresponding to the service call.

5. The electronic pharmacy adjudication system of claim 4, wherein processing the service call to identify in the data repository a data subset for use by the service call includes:
   a) processing the one or more decision rules to identify in the data repository a corresponding data subset for each decision rule amongst the one or more decision rules;
   b) executing each of the one or more decision rules at least in part by processing at least some of the set of parameters identified by the service call and the corresponding data subset.

6. The electronic pharmacy adjudication system of claim 1, wherein the rules repository includes one or more rules that apply to a specific insurance carrier, the one or more rules including rules selected from a set consisting of:
   a) core adjudication rules;
   b) legislative rules;
   c) rules pertaining to insurance programs developed by the specific insurance carrier and made available to all insurance carriers; and
   d) rules pertaining to insurance programs developed by the specific insurance carrier and only available to the specific insurance carrier.

7. The electronic pharmacy adjudication system of claim 1, wherein the service and rules engine layer is configured for:
   a) processing the service call to identify in the rules repository the one or more decision rules corresponding to the service call;
   b) executing the one or more decision rules identified in the rule repository to derive the partial decision result, wherein executing the one or more decision rules includes processing at least some of the set of parameters identified by the service call.

8. The electronic pharmacy adjudication system of claim 1, wherein the sequence of service calls generated by the orchestration layer includes one or more service calls selected from a set consisting of an eligibility verification service call, a benefit verification service call, a cost verification service call, a claim validation service call, and a claim persistence service call.

9. The electronic pharmacy adjudication system of claim 1, wherein said orchestration layer being configured for processing the information data elements in the at least 20,000 of the healthcare insurance claims to generate the sequence of service calls at least in part by:
   in response to receipt of the partial decision result corresponding to the first service call, selectively generating a second service call at least in part by processing the partial decision result corresponding to the first service call.

10. The electronic pharmacy adjudication system of claim 9, wherein the first service call includes an eligibility verification service call and wherein the second service call includes a benefit verification service call.

11. The electronic pharmacy adjudication system of claim 1, wherein the sequence of service calls includes the first service call and at least a second service call distinct from the first service call and wherein the orchestration layer being configured for forwarding the first service call to the service and rules engine layer prior to transmitting the second service call to the service and rules engine layer.

12. A method for performing an adjudication service in connection with healthcare insurance claims originating from a plurality of point of sale (POS) devices, each of the healthcare insurance claims including a plurality of information data elements specifying characteristics of the healthcare insurance claim, said method being implemented using one or more processors and a non-transitory computer readable memory storing computer program instructions, said method comprising:
   a) processing the information data elements in each of at least 20,000 of the healthcare insurance claims to generate a first service call in a sequence of service calls to derive a first partial decision in a sequence of partial decision results and processing the information data elements in each of the at least 20,000 of the healthcare insurance claims to generate one or more subsequent service calls in the sequence of service calls to derive one or more partial decisions in the sequence of partial decision results when an adjudication decision corresponding to a respective one of the at least 20,000 of the healthcare insurance claims cannot be derived from a previous partial decision result in the sequence of partial decision results corresponding to a previous service call in the sequence of service calls, wherein each service call in the sequence of service calls:
      i) identifies a set of parameters on which the service call is to be applied; and
      ii) corresponds to one or more decision rules in a rules repository, the one or more decision rules being a subset of decisions rules in the rules repository;
   b) processing the sequence of partial decision results to incrementally derive the adjudication decision corresponding to each of the at least 20,000 of the healthcare insurance claims;
   c) releasing results for transmittal over a data network to a respective one of the point of sale (POS) devices, the results conveying the derived adjudication decision corresponding to each of the at least 20,000 of the healthcare insurance claims.

13. The method of claim 12, wherein deriving a specific partial decision result in the sequence of partial decision results associated with a specific service call includes processing a specific set of parameters identified by the specific service call according to one or more specific decision rules from the rules repository, the one or more specific decision rules corresponding to the specific service call and being a specific subset of decisions rules in the rules repository.

14. The method of claim 13, wherein deriving the specific partial decision result in the sequence of partial decision results associated with the specific service call includes:
   a) processing the specific service call to identify in the rules repository the one or more specific decision rules corresponding to the specific service call;
   b) executing the one or more specific decision rules identified in the rule repository to derive the specific partial decision result, wherein executing the one or more specific decision rules includes processing at least some parameters in the specific set of parameters identified by the specific service call.

15. The method of claim 13, wherein deriving the specific partial decision result in the sequence of partial decision results associated with the specific service call includes:
    a) processing the specific service call to identify in a data repository a specific data set for use by the specific service call, the specific data set being a subset of data in the data repository;
    b) deriving the specific partial decision result at least in part by processing data in the identified specific data set and the specific set of parameters identified by the specific service call according to the one or more specific decision rules corresponding to the specific service call.

16. The method of claim 15, wherein processing the specific service call to identify in the data repository the specific subset of data for use by the specific service call includes:
    a) processing the one or more specific decision rules to identify in the data repository a corresponding specific data subset for each specific decision rule amongst the one or more specific decision rules;
    b) executing each of the one or more specific decision rules at least in part by processing at least some of the set of parameters identified by the specific service call and the corresponding specific data subset.

17. The method of claim 12, wherein the rules repository includes one or more rules that apply to a specific insurance carrier, the one or more rules including rules selected from the set consisting of:
    a) core adjudication rules;
    b) legislative rules;
    c) rules pertaining to insurance programs developed by the specific insurance carrier and made available to all insurance carriers; and
    d) rules pertaining to insurance programs developed by the specific insurance carrier and only available to the specific insurance carrier.

18. The method of claim 12, wherein the sequence of service calls includes one or more service calls selected from a set consisting of an eligibility verification service call, a benefit verification service call, a cost verification service call, a claim validation service call, and a claim persistence service call.

19. The method of claim 12, comprising processing the information data elements in the at least 20,000 of the healthcare insurance claims to generate the sequence of service calls is performed at last in part by:
    selectively generating a second service call at least in part by processing the first partial decision result corresponding to the first service call.

20. The method of claim 19, wherein the first service call includes an eligibility verification service call and wherein the second service call includes a benefit verification service call.

* * * * *